(12) United States Patent
Kourtakis et al.

(10) Patent No.: US 6,475,950 B2
(45) Date of Patent: Nov. 5, 2002

(54) CATALYTIC DEHYDROGENATION PROCESSES AND CHROMIUM CATALYSTS FOR USE THEREIN

(75) Inventors: Kostantinos Kourtakis, Media, PA (US); Leo E. Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/808,667

(22) Filed: Mar. 15, 2001

(65) Prior Publication Data

US 2001/0046942 A1 Nov. 29, 2001

Related U.S. Application Data

(60) Provisional application No. 60/189,772, filed on Mar. 16, 2000.

(51) Int. Cl.[7] .......................... B01J 23/00; C04B 35/03; C04B 35/04; C01G 37/14; C01G 37/02
(52) U.S. Cl. ................. 502/319; 502/305; 502/306; 502/307; 502/308; 502/310; 502/317; 502/320; 501/126; 501/127; 501/128; 501/132; 501/117; 423/595; 423/596; 423/607
(58) Field of Search ................. 502/305, 306, 502/307, 308, 310, 317, 319, 320, 323; 501/126, 127, 128, 117, 132; 423/61, 595, 596, 607; 252/519.1

(56) References Cited

U.S. PATENT DOCUMENTS

| | | | | | |
|---|---|---|---|---|---|
| 3,626,021 A | | 12/1971 | Michaels et al. | | |
| 3,686,347 A | * | 8/1972 | Dean et al. | ............. | 260/680 E |
| 3,879,525 A | * | 4/1975 | Miyata et al. | ............... | 423/277 |
| 3,907,715 A | * | 9/1975 | Arai et al. | .................... | 252/465 |
| 3,960,975 A | * | 6/1976 | Manning | .................... | 252/465 |
| 4,038,215 A | * | 7/1977 | Manning | .................... | 252/465 |
| 4,149,996 A | * | 4/1979 | Manning | .................... | 252/465 |
| 4,220,560 A | * | 9/1980 | Anquetil et al. | ............. | 252/468 |
| 4,308,175 A | * | 12/1981 | Erpenbach et al. | ......... | 252/458 |
| 4,337,028 A | * | 6/1982 | Angwin et al. | ................ | 431/7 |
| 4,351,814 A | * | 9/1982 | Miyata et al. | ............... | 423/306 |
| 4,454,244 A | * | 6/1984 | Woltermann | ................ | 502/208 |
| 4,476,243 A | | 10/1984 | Dombro | | |
| 4,513,162 A | | 4/1985 | Al-Muddarris | | |
| 4,668,491 A | | 5/1987 | Wimmer et al. | | |
| 4,788,174 A | * | 11/1988 | Arai | ........................... | 502/324 |
| 5,348,725 A | * | 9/1994 | Misra et al. | ................. | 423/594 |
| 5,356,730 A | * | 10/1994 | Minh et al. | ................... | 429/32 |
| 5,371,306 A | * | 12/1994 | Woo et al. | ................... | 568/804 |
| 5,378,350 A | | 1/1995 | Zimmermann | | |
| 5,627,295 A | * | 5/1997 | Sofianos et al. | ............... | 556/27 |

FOREIGN PATENT DOCUMENTS

| | | |
|---|---|---|
| EP | 947 247 | 10/1999 |
| FR | 1 333 360 | 12/1963 |
| FR | 2 748 021 | 10/1997 |
| GB | 1 007 709 | 10/1965 |

OTHER PUBLICATIONS

Weckhuysen, Bert M., Alkane Dehydrogenation Over Supported Chromium Oxide Catalysts, Catalysis Today 51 (1999) pp. 223–232.

* cited by examiner

*Primary Examiner*—Stuart L. Hendrickson
*Assistant Examiner*—Cam N. Nguyen

(57) ABSTRACT

A chromium catalyst is disclosed for use in dehydrogenation and dehydrocyclization processes.

8 Claims, No Drawings

US 6,475,950 B2

CATALYTIC DEHYDROGENATION PROCESSES AND CHROMIUM CATALYSTS FOR USE THEREIN

This application claims priority from Provisional application Ser. No. 60/189,772, filed Mar. 16, 2000.

FIELD OF THE INVENTION

The present invention relates to a novel catalyst comprising chromium and its use in dehydrogenation or dehydrocyclization of $C_2$-$_{10}$ hydrocarbon processes.

BACKGROUND OF THE INVENTION

The dehydrogenation of paraffins to olefins is commercially significant because of the need for olefins for the manufacture of high octane gasolines, elastomers, detergents, plastics, ion-exchange resins and pharmaceuticals. Important hydrocarbon dehydrocyclization reactions are the conversion of diisobutylene and isooctane to p-xylene.

Processes for the conversion of paraffin hydrocarbons to less saturated hydrocarbons are known. For example see U.S. Pat. No. 4,513,162, U.S. Pat. No. 5,378,350 and European Patent Application No. EP 947,247. Nonetheless, there is a continuing need to develop new catalysts which are more effective or otherwise improved for use in dehydrogenation processes.

SUMMARY OF THE INVENTION

Disclosed herein is a composition having the formula $Cr_aA_bB_c(O_{1-z}(OH)_{2z})_y$, wherein a+b+c=1; wherein A is an element selected from the group consisting of Zn, Sn, Rh, Li, Na, K, Rb, Cs, Be, Mg, Ca, Sr, Ce, and Ba; B is at least one element selected from the group consisting of Al, Si, and Mg; a is greater than 0.01 but less than 0.5; b is greater than 0.01 but less than or equal to 0.5; c is greater than 0.2 but less than or equal to 0.999; y is determined by the sum of the oxidation states of Cr, A and B individually multiplied by the corresponding stoichiometric coefficent a, b, c, said sum then divided by 2; and z is greater than or equal to 0 but less than or equal to 2.

This invention provides a process for converting at least one $C_2$ to $C_{10}$ hydrocarbon to less saturated hydrocarbons comprising the step of contacting at least one $C_2$ to $C_{10}$ hydrocarbon with at least one catalyst selected from the group consisting of $Cr_aA_bB_c(O_{1-z}(OH)_{2z})_y$, wherein A is an element selected from the group consisting of Zn, Sn, Rh, Li, Na, K, Rb, Cs, Be, Mg, Ca, Sr, Ce, and Ba; B is at least one element selected from the group consisting of Al, Si, and Mg; a+b+c=1; a is greater than 0.01 but less than 0.5; b is greater than 0.01 but less than or equal to 0.5; c is greater than 0.2 but less than or equal to 0.999; y is determined by the sum of the oxidation states of Cr, A and B individually multiplied by the corresponding stoichiometric coefficient (a, b, or c), and said sum then divided by 2; and z is greater than or equal to 0 but less than or equal to 2; with a catalyst composition comprising rhodium and rare earth oxides; at a temperature of about 300° C. to about 650° C.

DETAILED DESCRIPTION OF THE INVENTION

The catalyst compositions of the present invention are of the formula $Cr_aA_bB_c(O_{1-z}(OH)_{2z})_y$, wherein a+b+c=1; wherein A is an element selected from the group consisting of Zn, Sn, Rh, Li, Na, K, Rb, Cs, Be, Mg, Ca, Sr, Ce and Ba; B is at least one element selected from the group consisting of Al, Si, and Mg; a is greater than or equal to 0.01 but less than or equal to 0.5; b is greater than or equal to 0.01 but less than or equal to 0.5; c is greater than or equal to 0.2 but less than or equal to 0.999; y is determined by the sum of the oxidation states or Cr, A and B individually multiplied by the corresponding stoichiometric coefficent a, b, or c, said sum then divided by 2; and z is greater than or equal to 0 less than or equal to 2 can be prepared by a variety of known art methods such as impregnation, gel formation (including xerogel or aerogel formation), freeze-drying, spray drying, and spray roasting.

Impregnation

The impregnation technique typically comprises contacting a catalyst support with an aqueous solution of a compound of chromium and a solution of compounds containing elements A and/or B. For example, a water soluble chromium compound such as $Cr(NO_3)_3 \cdot 9H_2O$ can be impregnated into preformed oxides or oxyhydroxides of elements A and B (e.g., $MgSiO_3$). The contacting is followed by drying and calcining the supported materials. In some cases calcination can be accomplished in situ under reaction conditions.

Gel Formation

Pre-formed Colloidal Sol Destabilization: One or more inorganic metal colloids may be used as starting material for preparing the catalyst gels of the present invention. These colloids include colloidal alumina sols, colloidal silica sols or their mixtures. There are also several methods of preparing colloids, as described in "Inorganic Colloid Chemistry", Volumes 1, 2 and 3, J. Wiley and Sons, Inc., 1935. The pre-formed colloidal sols are sold commercially and readily available from Nyacol Products.

It is preferred that pre-formed colloidal sols in water, or aquasols, are used in the catalyst preparation for the dehydrogenation process invention disclosed herein. The aquasols are comprised of colloidal particles ranging in size from 2 nanometers to 50 nanometers. In general, the smaller primary particle sizes (2 nm to 5 nm) are preferred. The pre-formed colloidal sols contain from 10 to 35 weight % of colloidal oxides or other materials, depending on the method of stabilization.

In this invention, the colloids, which are originally stable heterogeneous dispersions of oxides and other species in solvents, are destabilized to produce colloidal gels. Destabilization is induced, in some cases, by the addition of soluble salts, (e.g., chlorides or nitrates), which change the pH and the ionic strength of the colloidal suspensions, by the addition of acids or bases, or by solvent removal. pH changes generally accompany the addition of soluble salts; in general, this is preferred over solvent removal. Generally, a pH range of from about 0 to about 12 can be used to destabilize the colloids. It is noted that very large extremes in pH (such as pH 12) can cause flocculation and precipitation. A pH range of from about 2 to 8 is generally preferred.

The medium used is typically aqueous, although non-aqueous colloids can also be used. The additional metal or inorganic reagents (i.e., salts of Cr or the A and B components) used should be soluble in the appropriate aqueous and non-aqueous media.

Sol-Gel Synthesis Using Alkoxides: The catalysts of the present invention can also be prepared by a sol gel process. One or more metal alkoxides (e.g., tetraethylorthosilicate)

may be used as starting material for preparing the gels. The inorganic metal alkoxides used to prepare the catalyst may include any alkoxide which contains from 1 to 20 carbon atoms, preferably 1 to 5 carbon atoms, in the alkoxide group. It is preferred that these alkoxides are soluble in the liquid reaction medium. $C_1$–$C_4$ alkoxides are most preferred. An example of a most preferred $C_1$–$C_4$ alkoxide is aluminum isopropoxide.

Commercially available alkoxides can be used. However, inorganic alkoxides can be prepared by other routes. Some examples include direct reaction of zero valent metals with alcohols in the presence of a catalyst. Many alkoxides can be formed by reaction of metal halides with alcohols. Alkoxy derivatives can be synthesized by the reaction of the alkoxide with alcohol in a ligand interchange reaction. Direct reactions of metal dialkylamides with alcohol also form alkoxide derivatives. Additional examples are disclosed in "Metal Alkoxides" by D.C. Bradley et al., Academic Press, (1978).

A solution of a soluble salt comprising at least one metal selected from the group consisting of Cr, Al, Zn, Sn, Rh, Li, Na, K, Rb, Cs, Be, Mg, Ca, Sr, Ce and Ba (e.g., $Cr(NO_3)_3$, chromium acetate, chromium hydroxide acetate, $Al(NO_3)_3$, $Zn(NO_3)_2$, $Sn(NO_3)_2$, $RhCl_3$, $LiNO_3$, $NaNO_3$, $KNO3$, $RbNO_3$, $CsNO_3$, $Be(NO_3)_2$, $Mg(NO_3)_2$, $Ca(NO_3)_2$, $Sr(NO_3)_2$, and $Ba(NO_3)_2$) is prepared. Other soluble salts (for example, acetates, chlorides, nitrates, nitrites) can also be used. An aqueous solution containing at least one dissolved metal salt is added to a non-aqueous solution of at least one alkoxide selected from the group consisting of magnesium, silicon, and aluminum alkoxides (e.g., magnesium methoxide, silicon tetraethylorthosilicate and aluminum isopropoxide) to induce a hydrolysis and condensation reaction of the alkoxides to form a gel. The solution is prepared in a moisture-free environment, preferably under inert conditions, for example a nitrogen blanket. It is also preferable that the hydrolysis reactions to induce gel formation be performed under a moisture free, inert gas, environment so that the hydrolysis can be controlled during the contacting step of the non-aqueous with the aqueous solutions. The material can be conventionally or supercritically dried to produce a xerogel or aerogel.

Alternatively, the catalysts of the present invention can also be prepared by a sol gel process using non-aqueous solvents. A solution of a soluble salt comprising at least one metal selected from the group consisting of Cr, Al, Si, Zn, Sn, Rh, Li, Na, K, Rb, Cs, Be, Mg, Ca, Sr, Ce and Ba soluble in non-aqueous media (e.g., Cr (acetylacetonate)$_3$, dissolved in ethanol and sodium ethoxide dissolved in ethanol) is prepared. A non-aqueous solution of at least one alkoxide selected from the group consisting of magnesium, silicon, and aluminum alkoxides (e.g., magnesium methoxide, silicon tetraethylorthosilicate and aluminum isopropoxide) is added to the soluble metal salt solution. The solution is prepared in a moisture-free environment, preferably under inert conditions, for example a nitrogen blanket. It is desirable to control hydrolysis and condensation by adding water so that one can induce gelation at the desired time. In a second step, water or other protic solutions (for example ethanol) optionally containing at least one dissolved metal selected from the group consisting of Cr, Al, Zn, Sn, Rh, Li, Na, K, Rb, Cs, Be, Mg, Ca, Sr, Ce and Ba, as described above, can be added to induce hydrolysis and condensation reactions to form a gel. It is also preferable that the hydrolysis reactions to induce gel formation be performed under a moisture free, inert gas environment so that the hydrolysis can be controlled during the contacting step of the non-aqueous with the aqueous solutions. The material can be conventionally or supercritically dried to produce a xerogel or aerogel.

The solution medium used to make the gel generally should be a solvent for the inorganic alkoxide or alkoxides used, and the additional metal reagents and promoters which are added in the synthesis. Solubility of all components in their respective media (aqueous and non-aqueous) is preferred. Solubility of all components results in highly dispersed materials, which in turn results in catalyst metal particles in the nanometer size range.

The addition of acidic or basic reagents to the inorganic alkoxide medium can have an effect on the kinetics of the hydrolysis and condensation, and the microstructure of the oxyhydroxide matrices derived from the alkoxide precursor which entraps or incorporates the soluble metal and promoter reagents. Generally, a pH within the range of from 1 to 12 can be used, with a pH range of from 1 to 6 being preferred.

In the preparation of the compositions of the present invention water and any aqueous solutions are added in a dropwise fashion to the alcohol soluble alkoxide and other reagents to induce hydrolysis and condensation. Depending on the alkoxide used, a discernible gel point can be reached in minutes or hours. The molar ratio of the total water added to total Mg, Si, and Al added (including water present in aqueous solutions) varies according to the specific inorganic alkoxide.

Typically, the concentration of the amount of solvent used is linked to the alkoxide content. For example, a molar ratio of 26.5:1 of alcohol (e.g., ethanol):total alkoxide can be used, although the molar ratio of alcohol:total alkoxide can be from about 5:1 to 53:1, or even greater. If a large excess of alcohol is used, gelation will not generally occur immediately; some solvent evaporation will be needed.

Generally, a molar ratio of water:alkoxide from about of 0.1:1 to 10:1 is used. The amount of water utilized in the reaction is that calculated to hydrolyze the inorganic alkoxide in the reaction mixture. A ratio lower than that needed to hydrolyze the alkoxide species will result in a partially hydrolyzed material, which in most cases will reach a gel point at a much slower rate, depending on the aging procedure and the presence of atmospheric moisture.

The xerogels and aerogels that are used for the catalysts of the present invention comprise a matrix material derived from a solution of the matrix component incorporating the active catalyst component, which is essentially derived from a dissolved component. A matrix is a skeletal framework of oxides and oxyhydroxides (also referred to as oxide/hydroxide) derived from the hydrolysis and condensation of alkoxides and other reagents. The framework typically comprises at least 20 mole % or more of the total catalyst composition. The matrix material comprises magnesium, silicon, or aluminum oxyhydroxides, xerogels or aerogels, or mixtures thereof totaling from about 20 mole % to about 99.9, preferably from 25 to 99 mole % of the catalyst composition.

The xerogels and aerogels thus produced can be described as precursor salts dispersed in an oxide or oxyhydroxide matrix. The hydroxyl content is at this point unknown. A theoretical maximum corresponds to the valence of central metal atom. The molar $H_2O$:alkoxide ratio can impact the final xerogel stoichiometry so that there will be residual —OR groups in unaged gel. However, reaction with atmospheric moisture will convert these to the corresponding —OH, and —O groups upon continued polymerization and dehydration. Aging, even under inert conditions, can also effect the condensation of the —OH, eliminating $H_2O$, through continuation of cross linking and polymerization, i.e., gel formation.

Catalysts disclosed herein can also be prepared by destabilizing pre-formed aquasols to form gels. For example, aqueous solutions of water soluble salts of Cr, Al, Zn, Sn, Rh, Li, Na, K, Rb, Cs, Be, Mg, Ca, Sr, Ce and Ba (e.g., $Cr(NO_3)_3$, $Al(NO_3)_3$, $Zn(NO_3)_2$, $Sn(NO_3)_2$, $RhCl_3$, $LiNO_3$, $NaNO_3$, $KNO_3$, $RbNO_3$, $CsNO_3$, $Be(NO_3)_2$, $Mg(NO_3)_2$, $Ca(NO_3)_2$, $Sr(NO_3)_2$, and $Ba(NO_3)_2$) are used. Other water soluble salts of Cr, Al, Zn, Sn, Rh, Li, Na, K, Rb, Cs, Be, Mg, Ca, Sr, Ce and Ba can be used (e.g., acetates, chlorides, nitrates, nitrites) also. These solutions are added to colloids such as a colloidal aluminum, silicon or magnesium aquasol to destabilize the aquasol by altering solution pH or ionic strength. Commercially available colloids may also be used. In some cases, the addition of acids (including nitric acid, acetic acid) or bases (including ammonium hydroxide) can also alter the pH of the solution and induce a gel point. The resulting gel must be dried. Subsequent drying steps can be performed be supercritical extraction or conventional drying to produce an aerogel or xerogel material.

The catalysts of the present invention can also be prepared by a sol gel process. Typically, magnesium, silicon, and aluminum alkoxides (including magnesium methoxide, silicon tetraethylorthosilicate, aluminum isopropoxide) are combined under an inert atmosphere. A controlled amount of aqueous solution containing salts selected from the group consisting of chromium Cr, Al, Zn, Sn, Rh, Li, Na, K, Rb, Cs, Be, Mg, Ca, Sr, Ce and Ba (e.g., $Cr(NO_3)_3$, chromium acetate, chromium hydroxide acetate, $Al(NO_3)_3$, $Zn(NO_3)_2$, $Sn(NO_3)_2$, $RhCl_3$, $LiNO_3$, $NaNO_3$, $KNO_3$, $RbNO_3$, $CsNO_3$, $Be(NO_3)_2$, $Mg(NO_3)_2$, $Ca(NO_3)_2$, $Sr(NO_3)_2$, and $Ba(NO_3)_2$) are used. Other water soluble salts (for example, acetates, chlorides, nitrates, nitrites) of Cr, Al, Zn, Sn, Rh, Li, Na, K, Rb, Cs, Be, Mg, Ca, Sr, Ce and Ba can be added to induce a gel point. The material can be conventionally or supercritcally dried to produce a xerogel or aerogel.

After forming the gels of the present invention, it may be necessary to complete the gelation process with some aging of the gel. This aging can range form one minute to several days. Generally, the gels are aged at room temperature in air for at least several hours.

Removal of solvent from the gels can be accomplished by several methods. Removal by vacuum drying or heating in air results in the formation of a xerogel. An aerogel of the material can typically be formed by charging in a pressurized system such as an autoclave. The gel containing the solvent is placed in an autoclave where it can be contacted with a fluid above its critical temperature and pressure. Various fluids can be used at their critical temperature and pressure for this purpose. For example, suitable fluids include fluorochlorocarbons typified by Freon® chlorofluorocarbons (e.g., Freon® 11 ($CCl_3F$), 12 ($CCl_2F_2$) or 114 ($CClF_2CClF_2$), ammonia and carbon dioxide.

Using Freeze Dying

Freeze drying procedures can accommodate several catalyst compositions, and are useful if the catalyst precursors are soluble in water or other solvent which can be rapidly frozen. Precursor salts are dissolved in an appropriate amount of solvent to form a solution or fine colloid. The solution is then rapidly cooled and frozen by immersion in a suitable medium, such as liquid nitrogen. If the solution is rapidly frozen, the salts and other components will remain intimately mixed and will not segregate to any significant degree. The frozen solid is transferred to a freeze drying chamber. The solution is kept frozen while water vapor is removed by evacuation. Refrigerated shelves are used to prevent thaw-out of the frozen solids during evacuation.

Freeze drying procedures for catalysts compositions in the present invention involve the use of soluble precursor salts. Solution concentrations can vary widely, and can range from 0.1 M to 10 M, depending on the solubility of the precursor salts used. Solutions are preferably rapidly frozen (<<1 min) to preserve intimate mixing of the precursor salt components. Evacuation times can vary from day(s) or week(s), depending on the quantity of solvent to be removed. Catalyst materials are typically calcined, either ex situ or in situ to produce the final, active form. Catalyst precursor solutions can also be soaked, added or impregnated into porous catalyst monoliths, frozen, dried and calcined as described above.

In a typical embodiment of the present invention, water soluble salts of Cr, Al, Zn, Sn, Rh, Li, Na, K, Rb, Cs, Be, Mg, Ca, Sr, Ce and Ba (e.g., $Cr(NO_3)_3$, $Al(NO_3)_3$, $Zn(NO_3)_2$, $Sn(NO_3)_2$, $RhCl_3$, $LiNO_3$, $NaNO_3$, $KNO3$, $RbNO_3$, $CsNO_3$, $Be(NO_3)_2$, $Mg(NO_3)_2$, $Ca(NO_3)_2$, $Sr(NO_3)_2$, and $Ba(NO_3)_2$) are used. The water-soluble salts are dissolved in water prior to freeze drying. Other water soluble salts of Cr, Al, Zn, Sn, Rh, Li, Na, K, Rb, Cs, Be, Mg, Ca, Sr, Ce and Ba (e.g., acetates, chlorides, nitrates, nitrites) and colloids of aluminum oxide, silicon oxide, or metal colloids containing Rh or Cr also can be used. Solution formation is preferable, but not required. Other solvent systems can be used, if they can be frozen. The solution is then rapidly frozen by immersion in a suitable medium, such as liquid nitrogen. When the resulting combination is frozen rapidly, the salts and other components will remain intimately mixed and, generally, will not segregate to any significant degree. The frozen solid is then dried under vacuum and optionally, heated in air, or calcined, to decompose the salt present. A freeze drying chamber may be used for drying.

Using Spray Dying

Spray drying procedures involve the use of solutions, colloids or slurries containing catalyst precursors or catalyst compounds. The technique consists of atomization of these liquids (usually but not exclusively aqueous) into a spray, and contact between spray and drying medium (usually hot air) resulting in moisture evaporation. The drying of the spray proceeds until the desired moisture content in the dried particles is obtain, and the product is recovered by suitable separation techniques (usually cyclone separation). A detailed description of spray drying methods can be found in "Spray Drying Handbook", $4^{th}$ edition by K Masters (Longman Scientific and Technical, John Wiley and Sons, N.Y.) c. 1985.

Using Spray Roasting

Spray roasting also involves the use of solutions or colloids, but generally involves drying and calcination (at higher temperatures) in one process step to produce catalyst powders.

Use of Disclosed Catalysts in Dehydrogenation Processes

The hydrocarbon feed that can be used in the present invention includes any $C_2$ to $C_{10}$ hydrocarbon with propane, isobutane and isooctane (2,2,4-trimethylpentane) being preferred. The process of the present invention can be carried out in fixed, moving, fluidized, ebullating or entrained bed reactors.

The catalysts of this invention can be periodically regenerated to remove coke. The regeneration is done by conventional techniques of carbon removal such as heating with an oxygen-containing gas, preferably air.

The gas hourly space velocity (GHSV) of the feed gas generally is in the range of from about 100 to about 3000 cc hydrocarbon feed/cc catalyst /hour, preferably from about 500 to about 1000 cc/cc/hour. The operating pressure is generally in the range of from about 7 kPa to about 700 kPa, preferably from about 7 kPa to about 400 kPa. The reaction temperature generally is in the range of from about 450° C. to about 800° C., preferably from about 500° C. to 600° C.

The less saturated hydrocarbon reaction products of this invention can be separated by conventional means such as distillation, membrane separation and absorption.

EXAMPLES

General Procedure for Catalyst Testing

Catalyst tests were performed in a fixed bed continuous flow quartz reactor with 6.4 mm id. The catalyst charge was 2.0 mL of −12/+20 mesh (−1.68/+0.84 mm) granules for Examples 1 to 5, 9 and Comparative Examples A and D; 1.0 mL of −12/+20 mesh (−1.68/+0.84 mm) granules for Examples 7, 8 and Comparative Examples B and C; 0.5 mL of −12/+20 mesh (−1.68/+0.84 mm) granules for Example 6. The reactor tube was heated in a tube furnace to 550° C. in flowing nitrogen until the temperature was stable. A thermocouple inside the catalyst bed was used to measure temperature. Once the desired temperature was achieved, a feed consisting of 50% isobutane/50% nitrogen (Examples 4 to 9 or a feed consisting of 50% propane/50% nitrogen (Examples 1, 2, 3) were passed over the catalyst bed. The contact time was 3.2 seconds for Examples 1, 2, 3, 7, 8, 9. The contact time was 1.6 seconds for Examples 4, 5, 6. The entire product stream was analyzed on-line using sampling valves and an HP5890 chromatogram (TCD)/HP 5971 mass selective detector.

The results of the catalyst tests are shown in Tables 1 (propane dehydrogenation), and 2 (isobutane dehydrogenation).

Legend

| | |
|---|---|
| $C_3$ is $CH_3CH_2CH_3$ | $C_3=$ is $CH_2=CHCH_3$ |
| iC4 is $(CH_3)_2CHCH_3$ | iC4= is $(CH_3)_2C=CH_2$ |
| Conv. is conversion | Sel. is selectivity |

EXAMPLES

Example 1

$Cr_{0.25}Zn_{0.25}Al_{0.5}$

A 1 M aqueous solution of $Cr(NO_3)_3 \cdot 9H_2O$ (23.346 mL) was simultaneously combined with an aqueous solution of $ZnCl_2$ (31.981 mL, 0.73 M), preformed $AlO_{1.5}$ aquasol (10.003 mL, 4.67 M) and 0.1 M HCl (4.660 mL). The material appeared gel-like within minutes. It was dried under vacuum for 5 hours (120° C.) and then calcined at 300° C. in air for 3 hours prior to use. The material was pelletized and granulated on −10/+20 mesh (−2.0/+0.84 mm) screens prior to use.

Example 2

$Rh_{0.01}Cr_{0.1}Ce_{0.89}$

A 0.02 M $RhCl_3$ solution (32 mL, prepared using 6 M HCl) was combined with a 2.5603 M (with respect to chromium) aqueous solution of $Cr_3(OH)_2(Ac)_7$ (2.45 mL) and a 0.7262 M cerium nitrate solution $(Ce(NO_3)_3 \cdot 6H_2O$, 78.14 mL). The material was frozen in liquid nitrogen and evacuated for at least five days prior to calcination. The powder was calcined at 525° C. in air for 1 hour. The material was pelletized and granulated on −10/+20 mesh (−2.0/+0.84 mm) screens prior to use.

Example 3

$Cr_{0.25}Al_{0.25}Sn_{0.5}$

The same procedure as described in Example 1 was used except that the following amounts of materials were used: 1 M aqueous solution of $Cr(No_3)_3 \cdot 9H_2O$ (24.879); 0.8438 M aqueous solution of $SnCl_2$ (29.485 mL, 0.73 M); preformed $AlO_{1.5}$ aquasol (10.66 mL, 4.67 M) and 0.1 M HCl (4.976 mL). The material appeared gel-like within minutes. It was dried under vacuum for 5 hours (120° C.) and then calcined at 300° C. in air for 3 hours. The material was pelletized and granulated on −10/+20 mesh (−2.0/+0.84 mm) screens prior to use.

Example 4

$Mg_{0.04}Cr_{0.2}Si_{0.76}$

A 0.699 M magnesium methoxide solution in methanol (12.856 mL) was added to a 150 mL petri dish along with tetraethylorthosilicate (60 vol. % in ethanol, 63.471 mL) and ethanol (6.125 mL) with gentle swirling. In a second step, a 2.5603 M (with respect to chromium) aqueous chromium hydroxide acetate (17.549 mL) was added. The material reached its gel point very quickly, and was dark purple in color. It was dried under vacuum for 5 hours (120° C.) and then calcined at 350° C. in air for 5 hours. The material was pelletized and granulated on −10/+20 mesh (−2.0/+0.84 mm) screens prior to use.

Example 5

$Cr_{0.2}Si_{0.8}$

An identical procedure as described in Example 4 was used with the following amounts of materials: 2.5603 M (with respect to chromium) aqueous chromium hydroxide acetate (20.344 mL); tetraethylorthosilicate (60 vol. % in ethanol, 77.455 mL). A homogeneous gel formed, which was dark purple in color. It was dried under vacuum for 5 hours (120° C.) and then calcined at 350° C. in air for 5 hours. The material was pelletized and granulated on −10/+20 mesh (−2.0/+0.84 mm) screens prior to use.

Example 6

$Rh_{0.01}Ce_{0.99}$

A solution of 0.02 M $RhCl_3$ (6.943 mL) (prepared by dissolving the salt in 6 M HCl) was added to an aqueous solution of 0.7261 M $Ce(NO_3)_3 \cdot 6H_2O$ (38.057 mL). The solution was rapidly frozen in liquid nitrogen, evacuated to drying on a freeze dryer, and the free flowing powder was calcined to 350° C. for 5 hours in air prior to use.

Example 7

$Cr_{0.25}Zn_{0.25}Al_{0.5}$

The Example 1 catalyst was used.

Example 8

$Rh_{0.01}Cr_{0.1}Ce_{0.89}$

The Example 2 catalyst was used.

Example 9

The Example 2 catalyst was used.

TABLE 1

PROPANE DEHYDROGENATION

| Ex. No. | % $C_3$ Conv. | % $C_3{=}$ Sel. | % $C_2$ Sel. | % $CH_4$ Sel. | % Others Sel. |
|---|---|---|---|---|---|
| 1 | 39.4 | 88.3 | 9.8 | 0.1 | 1.9 |
| 2 | 7.0 | 84.8 | 9.6 | 0 | 5.1 |
| 3 | 7.2 | 40.0 | 30.3 | 0 | 29.7 |

TABLE 2

ISOBUTANE DEHYDROGENATION

| Ex. No. | % $iC_4$ Conv. | % $iC_4{=}$ Sel. | % $CH_4$ Sel. | % $C_2$–$C_4$ Sel. | % Others Sel. |
|---|---|---|---|---|---|
| 4 | 45.5 | 84.1 | 8.9 | 7.1 | 0 |
| 5 | 54.0 | 82.1 | 9.6 | 8.4 | 0 |
| 6 | 13.1 | 42.4 | 18.8 | 38.9 | 0 |
| 7 | 72.6 | 56.7 | 18.5 | 23.5 | 1.4 |
| 8 | 15.3 | 83.5 | 0.6 | 14.7 | 1.3 |
| 9 | 11.6 | 51.3 | 3.0 | 25.3 | 20.5 |

What is claimed is:

1. A composition of matter having the formula $Cr_a A_b B_c (O_{1-z}(OH)_{2z})_y$, wherein a+b+c=1;

wherein A is an element selected from the group consisting of Zn, Sn, Rh, Li, Na, K, Rb, Cs, Be, Mg, Ca, Sr and Ba;

wherein B is at least one element selected from the group consisting of Al, Si and Mg;

wherein a is greater than 0.01 but less than 0.5; b is greater than 0.01 but less than or equal to 0.5; c is greater than 0.2 but less than or equal to 0.999;

wherein y is determined by the sum of the oxidation states of Cr, A and B individually multiplied by the corresponding stoichiometric coefficient a, b, or c, and said sum then divided by 2; and z is greater than or equal to 0 but less than or equal to 2, and when z is greater than 1, the composition contains no oxygen as oxide.

2. A composition of claim 1 wherein said composition is prepared from $C_1$–$C_{20}$ metal alkoxides.

3. The composition of claim 1 wherein said composition is prepared from $C_1$–$C_4$ metal alkoxides.

4. The composition of claim 3 wherein the composition is prepared from aluminum isopropoxide.

5. A process of making the composition of claim 1, said process comprising:

preparing a solution of a soluble salt comprising at least one metal selected from the group consisting of Cr, Al, Sn, Rh, Li, Na, K, Rb, Cs, Be, Mg, Ca, Sr and Ba;

adding said solution to a non-aqueous solution of a soluble salt comprising at least one metal selected from the group consisting of Cr, Al, Si, Zn, Sn, Rh, Li, Na, K, Rb, Cs, Be, Mg, Ca, Sr, and Ba to form a gel;

drying said gel to produce a xerogel or aerogel.

6. A process for making the composition of claim 1, said process comprising:

preparing a non-aqueous solution of a soluble salt comprising at least one metal selected from the group consisting of Cr, Al, Si, Zn, Sn, Rh, Li, Na, K, Rb, Cs, Be, Mg, Ca, Sr and Ba and at least one alkoxide selected from the group consisting of magnesium, silicon, and aluminum alkoxides in an inert atmosphere;

adding water or other protic solvents, optionally containing at least one dissolved metal selected from the group consisting of Cr, Al, Zn, Sn, Rh, Li, Na, K, Rb, Cs, Be, Mg, Ca, Sr, and Ba, to form a gel; and drying said gel to produce a xerogel or aerogel.

7. A process of making the composition of claim 1, said process comprising:

contacting a solution comprising water soluble salt selected from the group from the group consisting of Cr, Al, Zn, Sn. Rh, Li, Na, K, Rb, Cs, Be, Mg, Ca, Sr, and Ba with a colloid selected from the group consisting of magnesium, aluminum and silicon;

optionally, adding a pH altering solution whereby the colloid is destabilized;

optionally, removing solvent whereby the colloid is destabilized; and drying said gel to produce a xerogel or aerogel.

8. A process of making the composition of claim 1 said process comprising:

combining, in the presence of chromium, a solution comprising at least one of element A and at least one of element B to form a solution or a suspension;

freezing rapidly the combination of the first step;

drying the frozen solid under vacuum; and optionally, heating the resulting solid to decompose the salts.

* * * * *